United States Patent [19]

Sperling et al.

[11] Patent Number: 5,314,664
[45] Date of Patent: May 24, 1994

[54] SAMPLE SUPPLY SYSTEM HAVING INTEGRATED MICROWAVE DISINTEGRATION

[75] Inventors: Michael Sperling, Sipplingen; Dimiter L. Tsalev, Bulgarien, both of Fed. Rep. of Germany

[73] Assignee: Bodenseewerk Perkin-Elmer GmbH, Überlingen, Fed. Rep. of Germany

[21] Appl. No.: 861,751

[22] Filed: Apr. 1, 1992

[30] Foreign Application Priority Data

Apr. 3, 1991 [DE] Fed. Rep. of Germany ....... 4110735

[51] Int. Cl.$^5$ .............................................. G01N 1/00
[52] U.S. Cl. ..................................... 422/78; 422/21; 422/68.1; 422/81; 436/171; 436/173; 436/175; 219/718
[58] Field of Search ................... 422/52, 68.1, 78, 70, 422/102, 103, 242, 21, 81; 436/114, 115, 171, 173, 175; 219/10.55 A, 10.55 R

[56] References Cited

U.S. PATENT DOCUMENTS

| | | | |
|---|---|---|---|
| 3,967,931 | 7/1976 | Juvet, Jr. et al. | 422/70 X |
| 4,114,011 | 9/1978 | Stubbs | 219/10.55 M |
| 4,174,772 | 11/1979 | Neuss et al. | 435/32 |
| 4,352,780 | 10/1982 | Schick | 422/67 |
| 4,358,652 | 11/1982 | Kaarup | 219/10.55 A |
| 4,448,691 | 5/1984 | Davis | 422/70 X |
| 4,816,226 | 3/1989 | Jordan et al. | 422/81 |
| 4,861,556 | 8/1989 | Neas et al. | 422/78 |
| 4,882,286 | 11/1989 | Neas et al. | 436/175 |
| 4,946,797 | 8/1990 | Neas et al. | 436/175 |
| 5,045,196 | 9/1991 | Fang et al. | 210/278 |
| 5,061,638 | 10/1991 | Guter | 436/110 |
| 5,071,624 | 12/1991 | Sperling | 422/69 |
| 5,098,658 | 3/1992 | Huber | 422/78 |

FOREIGN PATENT DOCUMENTS

| | | |
|---|---|---|
| 3842315 | 6/1990 | Fed. Rep. of Germany . |
| 3917956 | 12/1990 | Fed. Rep. of Germany . |
| 1308940 | 12/1989 | Japan . |
| 2099579 | 12/1982 | United Kingdom . |

OTHER PUBLICATIONS

Haswell et al, On-line Microwave Disgestion of Slurry Samples With Direct Flame Atomic Absorption Spectrometric Elemental Detection, Analyst, Feb. 1992, vol. 117, pp. 117-120.

Aoyagi et al, Rapid Spectrophoto Metric Determination of Total Phosphorus in Industrial Wastewaters By Flow Injection Analysis Including a Capillary Digestor, Analytica Chimica Acta, 214 (1988) 229-237, Amsterdam.

Chen et al. Preparative Scale Organic Synthesis Using a Kitchen Microwave Oven, J. Chem. Soc. Chem. Common 1990, pp. 807-809.

Hirai et al, Flow Injection Analysis of Inorganic Polyphosphates, Analytica Chimica Acta, 115 (1980) 269-277.

Backstrom et al, Sample Work-Up for Graphite Furnace Atomic-absorption Spectrometry Using Continuous Flow Extraction, in Analyst, Mar. 1984, vol. 109, pp. 323-325.

(List continued on next page.)

Primary Examiner—James C. Housel
Assistant Examiner—Harold Y. Pyon
Attorney, Agent, or Firm—Edwin T. Grimes

[57] ABSTRACT

The flow-injection system includes a microwave oven having a flow-through reactor having a flow-through conduit located in windings around a conduit carrier for absorbing microwaves. The windings extend through the radiation cavity of the microwave oven only with a part of their length and transversely to the radiation direction. The microwave oven includes programmable adjusting means for the heating power and the heating period. Thus, in connection with a reduction flow-through reactor and an atomic absorption spectrometer, a determination of hydride formers and mercury in a material sample is possible, independently of the valence state.

14 Claims, 4 Drawing Sheets

OTHER PUBLICATIONS

Goto et al, Continuous micro flow monitoring method for total mercury at sub-ppb level in wastewater and other waters using cold vapor atomic absorption Spectrometry, in Fresenius Z Anal Chem (1988) 332: 745–749.

Ruzicka et al, Homogeneous and Heterogeneous Systems-Flow Injection Analysis Today and Tomorrow, in Analytica Chimica Acta, 214 (1988) 1–27.

Broekaert, Die FlieBinjektionsanalyse (FIA) in der Atomspektrometrie, in Nachr. Chem Tech lab 39 (1991) Nr. 3, pp. 310–315.

Hinkamp et al, Determination of total phosphorus in waters with amperometric detection by coupling of flow-injection analysis with continuous microwave oven digestion, in Analytica Chimica Acta, 236 (1990), 345–350.

Burguera et al, Flow Injection and Microwave-Oven sample decomposition for Determination of Copper, Zinc, and Iron in Whole Blood by Atomic Absorption Spectrometry, in Analytica Chimica Acta, 179 (1986) 351–357.

SAMPLE SUPPLY SYSTEM HAVING INTEGRATED MICROWAVE DISINTEGRATION

TECHNICAL FIELD

The invention relates to a system for disintegrating samples and for supplying the disintegrated samples to an analytical instrument, comprising
(a) a microwave oven having a radiation cavity and containing a flow-through reactor having an inlet and an outlet,
(b) pump means for pumping a mixture of sample and a disintegrating agent through said flow-through reactor,
(c) said reactor outlet being adapted to be connected to sample inlet means of said analytical instrument.

BACKGROUND ART

U.S. Pat. No. 5,071 624 discloses an arrangement for the enrichment of sample substances for spectroscopical purposes in a flow-injection analysis, wherein an ion exchange column is used for the enrichment. In this arrangement the flow-injection means serve to apply the sample substance to the ion exchange column, to elute it therefrom in enriched form and to supply it to sample feeding means in the form of a dosing capillary tube.

From the dosing capillary tube, the enriched sample is dispensed into a tubular furnace of an atomic absorption spectrometer.

In this arrangement, the flow-injection can only be used for the supply of the sample substance. Sample treatment, particularly sample disintegration, is not provided.

Furthermore, numerous arrangements for use in flow-through analysis are known. Thus, U.S. Pat. No. 5,045,196 shows an ion exchange column. German patent document 3,833,248 shows a device for supplying a well-defined sample volume to an instrument. A paper by Jaramier Rudzicker, "Homogeneous and Heterogeneous Systems Flow Injection Analysis Today and Tomorrow", in "Analytica Chimica Acta", 214 (1988), pp. 1–27 shows a pump arrangement for admixing. German patent 3,606,938 shows a diaphragm type admixing device. German patent 2,842,864 shows a device for flow extraction, wherein one substance is solved in a first solvent phase and is extracted with a second solvent phase, which is unmixable with the first solvent phase. German utility model 90 13 193 shows the modular construction of a flow-injection analysis system.

British patent document 2,099,579 discloses the use, in flow-injection systems of components which consist of polytetrafluorethylene. A paper "Die FlieBinjektionsanalyse (FIA) in der Atomspektrometrie" in "Nachrichten chemische Technik LAB" 39 Nr. 3 (1991), pp. 310–315 discloses the use of atomic spectrometers, atomic absorption spectrometers and flame atomic absorption spectrometers as analytical instruments in flowinjection analysis. From European patent document 0,212,241, it is known to direct volatile hydrides optionally to a plasma emission instrument or to a heated measuring cuvette for the atomic absorption spectroscopy. In this respect, furthermore, the paper by Masashi Goto et al. "Continuous micro flow monitoring method for total mercury at sub-ppb level in wastewater and other waters using cold vapor atomic absorption spectrometry" in Fresenius Z Anal. Chem. Jg. 332(1988) pp. 745–749 is to be mentioned. The use of atomic absorption spectrometers as analytical instruments in flow-injection systems is also known from a paper by Backstrom, Kenneth and Danielsson, Lars-Goran: "Sample Work-up for Graphite Furnace Atomic-absorption Spectrometry" Vol. 109, March 1984, pp. 323–325. A paper by Mertens, H and Althaus, A "Bestimmung von Quecksilber mit Hilfe der Amalgamtechnik unter Verwendung von Hydroxylammoniumchlorid und Natriumborhydrid oder Zinn(II)-chlorid" in "Fresenius Z Anal. Chem." Issue 7, 983, pp. 696–698 discloses the use of aerosol separators in the inert gas flow and the use of mercury adsorbers. Disclosure in this respect is also contained in German patent document 3,917,956, German patent document 3,503,315 and U.S. Pat. No. 4,816,226.

It is also known to use microwave ovens in analytical techniques for the disintegration of a sample. Thus, U.S. Pat. No. 4,946,797 describes the use of a microwave oven for wet disintegration in the determination of nitrogen according to Kjeldahl. From JP 1-308940 A in "Patent Abstracts of Japan" P-1014, Feb. 28, 1990, Vol 14/no 11, it is known to use a microwave oven in gas or liquid chromatography for treating a mixture, which has previously been treated with ultrasonics.

From the paper by M. Burgurea and J. L. Burgurea in Analytica Chimica Acta 179 (1986), pages 351 to 357 under the title "Flow-injection and microwave-oven sample decomposition for determination of copper, zinc and iron in whole blood by atomic absorption spectroscopy" it is known to use a microwave oven in connection with flow-injection in order to disintegrate a sample for the subsequent measurement of the atomic absorption. To this end, the flow-injection system comprises a double valve by means of which a blood sample and a disintegrating agent, namely a mixture of hydrochloric acid and nitric acid, are injected into separate carrier liquid flows which are combined at the inlet of a flow-through reactor. The microwave oven is a normal household appliance, and the flow-through reactor forms a tubular conduit of pyrex which is wound to a coil and arranged in the radiation cavity of the microwave oven. After having passed through the flow-through reactor, the disintegrated sample is introduced into the nebulizer of a flame atomic absorption spectrometer.

In this publication it is explained that the volumes of the sample and of the disintegrating agent as well as the length of the pyrex tube and the flow rate have to be adjusted such that the dwell time in the microwave oven, on one hand, is sufficent for the complete disintegration of the sample and, on the other hand, is not so long that steam or gas bubble formation in the liquid is caused in the flow-through reactor. Such steam or gas bubble formation has a negative effect on the flow-injection analysis because it results in nonreproducible dispersion, i.e. means mixture of the sample with the carrier liquid.

In a paper by S. Hinkamp and G. Schwedt in Analytica Chimica Acta 236 (1990), pages 345 to 350, under the title "Determination of total phosphorus in waters with amperometric detection of total coupling of flow-injection analysis with continuous microwave oven digestion", a microwave oven is described in connection with a flow-through reactor. The flow-through reactor consists of a tubular conduit of polytetrafluorethylene wound to a coil, on the inlet side of which a carrier liquid flow with water samples containing phosphate is combined with a flow of disintegrating agent. Here, the disintegrating agent consists of a solution of peroxodisulphate or perchloric acid, through which all of the phosphorous compounds are transformed into the orthophosphate at the pH of the carrier liquid The microwave oven which likewise is a household appliance, further includes a water cooler.

After the transformation in the flow-through reactor, the carrier liquid flow passes through a gas diffusion cell in which gas bubbles are removed from the liquid flow. Subsequently, the carrier liquid flow with the disintegrated sample is combined with a reagent flow (acid ammonium molybdate solution) in a further flow-through reactor and subsequently gets into an electrochemical gauge head in which the formed molybdophosphate is reduced amperometrically to molybdenum blue and, thus, the contents of phosphate is determined in the sample.

Microwave ovens of the type used as household appliances have a power of 650 Watt and, thus, they are considerably overdimensioned with regard to the relatively small liquid quantities which have to be heated in flow-injection analysis. As can be seen from the illustration in FIG. 1, very low microwave powers are sufficient to heat the liquid in the microwave oven to the desired disintegration temperature. FIG. 1 shows the achievable liquid temperature in the form of the temperature difference $\Delta T$ in °C. relative to ambient temperature as a function of the flow rate and the irradiated microwave power. It can be seen that only small fractions of the total power of 650 Watt are required in order to achieve the desired disintegration temperature. At the same time, however, also the problem arises that disintegration reactions also at higher temperatures need a certain minimum of time in order to definitely complete the desired disintegration, because otherwise the analysis result is falsified. These problems are additionally complicated in that the required disintegration temperatures and disintegration times depend on the matrix which is contained in the element to be determined. Thus, all in all, a high variability in the adjustment of the disintegration conditions is required, because the disintegration conditions vary from sample to sample. This variability is not present in the known devices, because, due to the high power of the microwave ovens, certain conditions with regard to conduit diameter and flow rate have to be maintained in order to avoid overheating and the vapour and gas bubble formation resulting therefrom, which would cause an unreproducible dispersion. Then, also additional means for removing the vapour and gas bubbles would have to be provided.

SUMMARY OF INVENTION

Accordingly, it is an object of the invention to provide a flow-injection system of the type described above, wherein overheating of the liquid flow in the flow-through reactor is avoided and the required adaptation to different disintegration conditions is possible.

According to the invention, this object is achieved with a system of the type defined in paragraphs (a); (b); (c) above, in that
(d) said flow-through reactor including a flow-through conduit coil, and
(e) said flow-through conduit coil having a first portion of its length extending into said radiation cavity and a second portion located outside said radiation cavity, whereby said mixture of sample and disintegrating agent flowing through said flowthrough conduit coil in each turn of said conduit coil alternately passes through a portion of this turn located inside said radiation cavity, where it is heated by the microwave energy of said oven, and through a portion of this turn outside said radiation energy where it is not heated.

In this way the flowing liquid stays in the microwave oven for a dwell time which is sufficient for the complete disintegration, without, however, being subjected to the risk of overheating and forming vapor and gas bubbles. This is due to the fact that the liquid does not stay in the radiation cavity of the microwave oven for the whole dwell time.

Preferably said flow-through conduit forms a conduit coil around said conduit carrier.

The system may further comprise a first ballast conduit coil arranged in said radiation cavity in addition to said flow-through reactor pump means for pumping a microwave-absorbing fluid through said ballast conduit coil.

In this way, a "thermal ballast" is provided, which absorbs a substantial part of the generated microwave energy and, thereby, prevents "dry-run" of the microwave oven.

Preferably, a beam of microwave radiation in said microwave oven irradiates said radiation cavity substantially along a first axis, said conduit coil of said flow-through reactor being wound about an axis parallel to said first axis, whereby the conduit of said conduit coil is substantially transverse to said first axis.

As the conduit extends transversely to the beam of microwave radiation, the liquid flow absorbs comparatively little microwave energy when passing through the radiation cavity.

In contrast thereto, said ballast conduit coil is wound about a second axis orthogonal to said first axis, whereby a major portion of said ballast conduit coil extends along said beam of microwave radiation.

In this way, substantially the whole length of the ballast conduit coil is located within the beam of microwave radiation.

The microwave oven, in the system of the invention can easily be adapted to quite different disintegration conditions without any risk of vapor or gas bubble formation due to overheating of the liquid flow. The microwave oven preferably is provided with programmable adjusting means for adjusting the heating power and heating period.

The system may comprise flow-injection means for injecting sample liquid into a flow of carrier liquid, said flow of carrier liquid being pumped by said pump means through said flow-through reactor.

With particular advantage, the system of the invention can be used in combination with an atomic absorption spectrometer for determining elements forming volatile hydrides or for determining mercury.

To this end, the system further comprises
(a) a reduction flow-through reactor having an inlet and an outlet, said inlet of said reduction flowthrough reactor communicating with the outlet of said flow-through reactor in said microwave oven, and
(b) means for supplying a reducing agent to said inlet of said reduction flow-through reactor, said outlet of said reduction flow-through reactor being adapted to be connected to sample inlet means of said atomic spectrometer.

Preferably, there are means for supplying an inert gas flow to said reduction flow-through reactor and an aerosol trap interconnected between said outlet of said reduction flow-through reactor and said sample inlet means.

For detecting mercury, the system further comprises a mercury absorber interconnected between said aerosol trap and said sample inlet means.

The reduction flow-through reactor is connected to an inert gas source. The inert gas is to convey the volatile hydrides or mercury vapor. The outlet of the reduction flow-through reactor is connected to the aerosol trap, whereby the gases are separated from the liquid and are supplied, for example, to the atomic absorption spectrometer.

According to a preferred design, said conduit carrier is an elongated body extending along a second axis normal to said first axis, said conduit coil being wound lengthwise on said elongated body, whereby the mayor portion of said conduit is parallel to said second axis. To this end, (a) said elongated conduit carrier has generally rectangular cross section normal to said second axis,
(b) said conduit carrier having a section, along said second axis, wherein the cross section has reduced dimensions,
(c) said lengthwise conduit coil of said flow-through reactor spanning said reduced dimensions section and
(d) said ballast conduit coil being wound about said reduced dimension section inside said conduit coil of the flow-through reactor.

BRIEF DESCRIPTION OF THE DRAWINGS

Embodiments of the invention will now be described in greater detail with reference to the accompanying drawings.

PREFERRED EMBODIMENTS OF THE INVENTION

Figure 1:
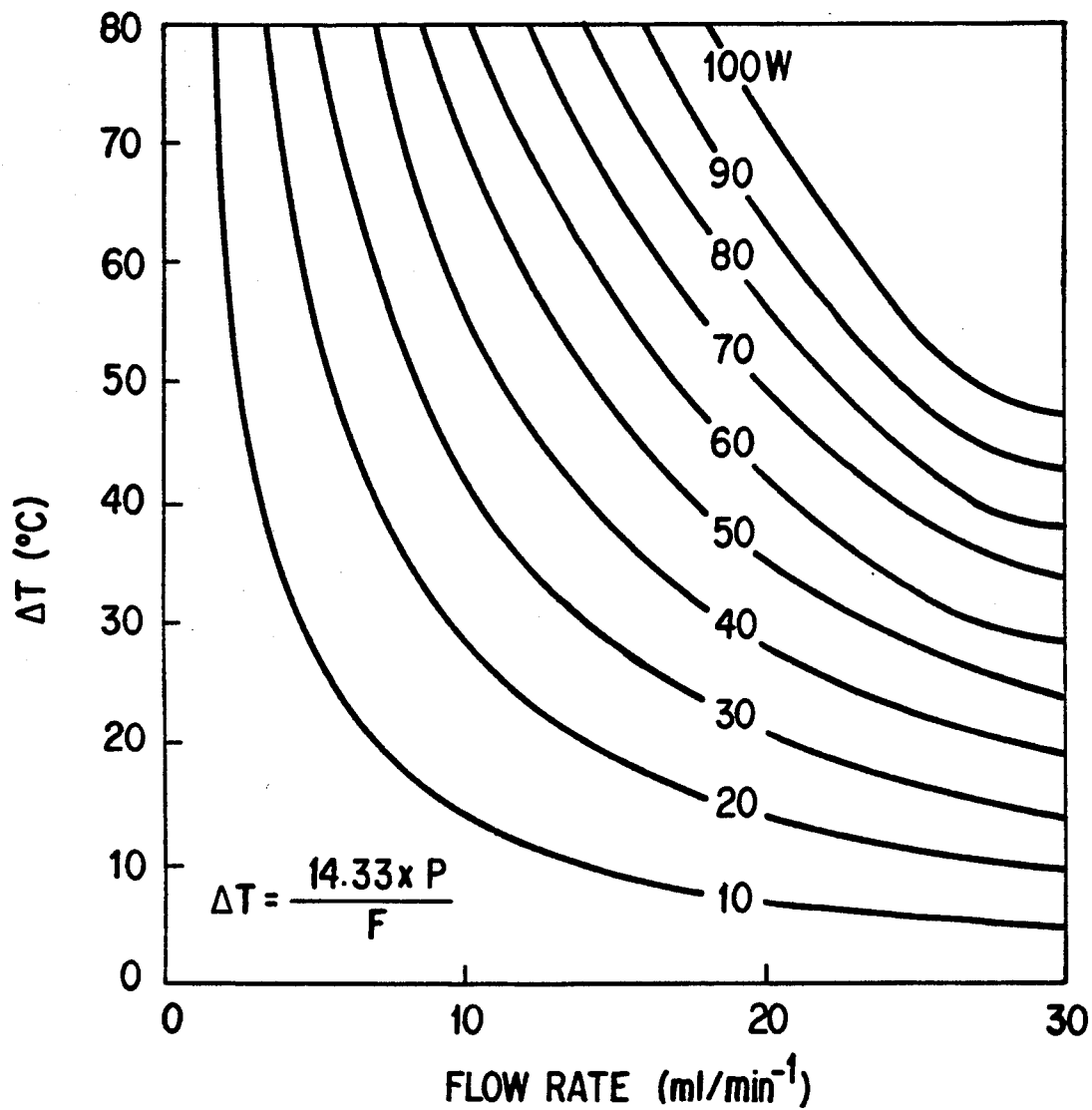
FIG. 1 is a schematic diagram, in which the temperature increase of a liquid flow in a microwave oven is illustrated as a function of the flow rate and the microwave power.
Figure 2:
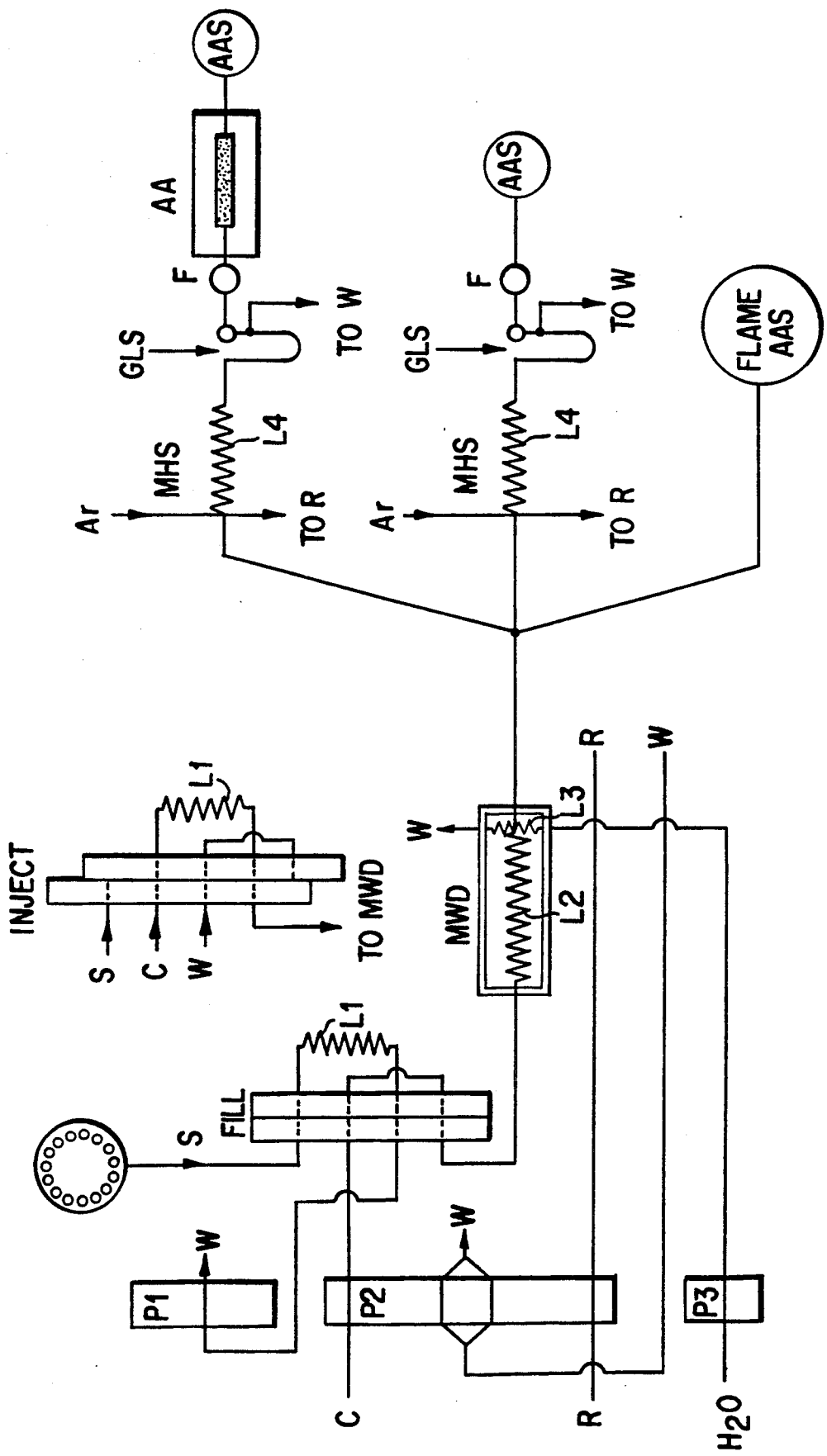
FIG. 2 is a schematic illustration of the flow injection system of the invention in connection with an atomic absorption spectrometer.

In the left half of FIG. 2, a flow-injection system is schematically illustrated, which consists of conventional components and can be used in combination with very different analytical instruments. A microwave oven MWD for sample disintegration is integrated in the system.

An autosampler S of conventional design, for example a Perkin-Elmer AS-90 autosampler, is associated with the flow-injection system. In this autosampler S sample vessels for the samples to be analyzed are arranged in a circular array on a turntable Furthermore, the flowinjection system is provided with a pump arrangement for feeding the different liquids. A pump P1 of this pump arrangement coacts with a sample injection valve having a sample loop L1. The sample loop is filled with sample liquid from the sample vessel present at the time The associated conduit leads to a waste vessel W.

A pump P2 of the pump arrangement is connected, on its inlet side, to a supply of a carrier liquid C and, on its output side, to a conduit L which leads to the microwave oven MWD. The sample injection valve is connected into this conduit L. The conduit L leads to the flow-through reactor L2 of the microwave oven MWD and, from there, finally likewise to the waste vessel W. The pump P2 feeds the carrier liquid through the conduit L. When the sample injection valve is actuated, the metered sample volume present in the sample loop L1 is injected into the carrier liquid flow and is conveyed thereby into the microwave oven MWD.

In the illustrated embodiment, the sample present in the sample vessel of the autosampler S has already been mixed with a suitable disintegrating agent such that the sample injected into the carrier liquid current is fed together with the disintegrating agent through the the conduit L. However, instead the pump P2 and the sample injection valve can be constructed as double element which injects the disintegrating agent and the sample separately into two carrier liquid flows which are combined in the conduit L before entrance into the microwave oven MWD. This is similar to the above mentioned publication by Burgurea et. al. In the end, the disintegrating agent and the sample are supplied to the microwave oven MWD.

The microwave oven MWD contains a flow-through reactor L2. The reactor L2 is connected, on the inlet side, to the conduit L. Furthermore, a "thermal ballast" is provided in the microwave oven MWD. This "thermal ballast" takes up and carries off the main part of the irradiated microwave energy and prevents a dry-run of the microwave oven MWD. If the supply of the carrier liquid through the flow-through reactor L2 is interrupted then, without such ballast, all of the carrier liquid would evaporate. In the illustrated embodiment this thermal ballast is formed by a conduit coil L3. Water is pumped through conduit coil L3 by means of a further pump P3 of the pump arrangement. This water, likewise, is drained to the waste vessel W. Instead of water, also another medium strongly absorbing microwaves can be pumped through this conduit coil L3 by the pump P3.

Figure 3B:
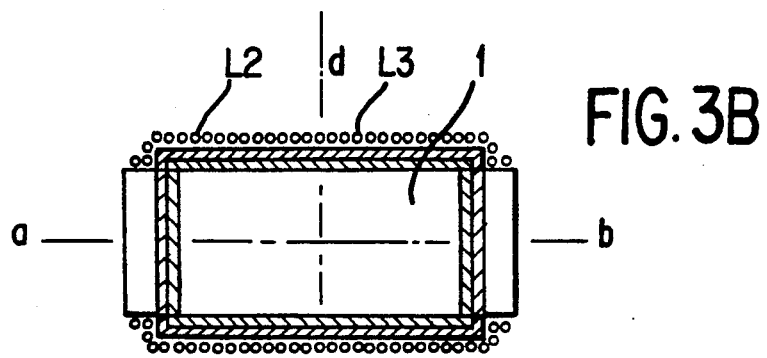
FIG. 3A and 3B are a longitudinal sectional view and a cross-sectional view, respectively, through the flow-through reactor in the flow-injection system of FIG. 2.
Figure 3A:
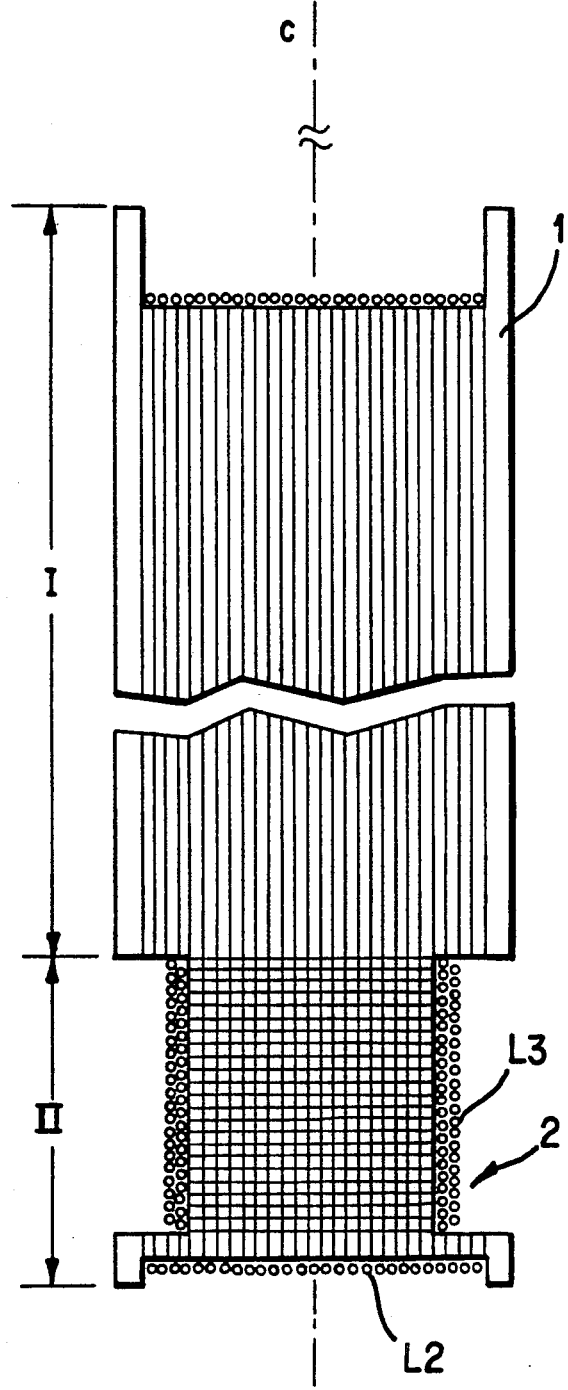

The arrangement of the flow-through reactor L2 and the conduit coil L3 of the microwave oven is illustrated in detail in longitudinal section in FIG. 3A and in crossection in FIG. 3B. The microwave oven MWD comprises a longitudinal conduit carrier 1 of a material absorbing microwaves only a little, for example polytetrafluorethylene. Only part of the length of the conduit carrier 1 extends into the radiation cavity of the microwave oven MWD. This part is an end part of reduced cross sectional area. The major part of the length of carrier 1 is arranged outside this radiation cavity. The flow-through reactor L2 forms a flow-through conduit which is wound as a coil with a number of turns longitudinally around the conduit carrier 1. In the illustrated embodiment the flow-through reactor L2 forms a single-layer coil of a hose conduit. Thus, each turn of this coil is located in the radiation cavity of the microwave oven MWD only with that portion of its length which extends across the end part 2 of reduced cross sectional area.

The end part 2 of the conduit carrier 1 is provided with a plurality of turns of the conduit coil L3. In the illustrated embodiment, the turns are wound in two layers around the end part 2 about an axis (vertical in FIG. 3A), which is normal to the axis (horizontal in the paper plane in FIG. 3A) about which the conduit coil L2 is wound. Thus, the turns of the conduit coil L3 and the turns of the flow-through reactor L2 are mutually perpendicular. Only the turns of the conduit coil L3 are located with their total lengths in the radiation cavity of the microwave oven MWD.

In the cross-sectional illustration of FIG. 3B it can be seen that the conduit carrier 1 has rectangular crosssection. For reasons of better clarity, here the layers of the windings of the conduit coil L3 are hatched in FIG. 3B. In this Figure, the radiation direction of the microwave oven MWD is indicated by a-b. From this illustration it can directly be seen that the turns of the conduit coil L3 extend in the radiation cavity such that the medium which strongly absorbs microwaves and flows through the conduit coil L3, is subjected to the microwaves over the total length of the turns. It can likewise be seen that the turns of the flow-through reactor L2 are subjected to the microwaves just over the part of its length which extends longitudinally of the conduit carrier 1 over the end part 2, and extend transversely to the radiation direction a-b in the direction c-d.

Thus, it turns out that the liquid, when passing through the coil of the flow-through reactor L2, is heated only intermittently by the microwave radiation such that no overheating with vapour and gas bubble formation occurs even with extended dwell time. However, the medium strongly absorbing microwaves in the turns of the conduit coil L3 is located in the radiation cavity of the microwave oven during the total dwell time and, thus, is always subjected to the heating by the microwaves. Through this arrangement, the desired function as thermal ballast is excellently fulfilled.

The conduit carrier 1 with the flow-through reactor L2 and the conduit coil L3 is supported by conventional means on the housing of the microwave oven MWD. Standard port means are provided for connection of the flow-through reactor L2 and the conduit coil L3 on their inlet and outlet sides to the respective conduits. In the embodiment the microwave oven MWD is a MX 350 Maxidigest microwave station of Prolabo, which is provided with programmable adjusting means (TX 31 Maxidigest Programmer), which enable adjustment of the operating conditions, particularly with respect to the heating capacity and the heating period to permit adaptation to the respective disintegration requirements.

After having passed through the microwave oven MWD, the carrier liquid flow with the disintegrated sample can be supplied to the sample inlet means of the respective analytical instrument. The analytical instrument can, for example, be an atomic spectrometer, such as an atomic emission spectrometer, but also an atomic absorption spectrometer, such as the flame atomic absorption spectrometer described in the above mentioned paper by Burgurea et. al., the liquid current being directly supplied to the nebulizer of the instrument.

In a preferred embodiment, the above described flow-injection system is operated with an atomic absorption spectrometer AAS which is designed for determination of mercury and hydride formers, that means of volatile elements or such elements which form volatile hydrides. To this end, the atomic absorption spectrometer AAS is provided with a quartz cuvette in which the atomic absorption of elementary mercury is measured. The quartz cuvette is heatable, in order to thermally decompose the hydrides introduced into the quartz cuvette by the sample inlet means and to measure the atomic absorption of the respective element. Such element may for example be tin, lead, arsenic, antimony, bismuth, selenium or tellurium.

For this purpose, it is necessary, after the sample disintegration, to transform the above mentioned elements into the volatile form and convey them in an inert gas flow. This is achieved by the arrangement schematically illustrated in the right half of FIG. 2. The components of this part of the flow-injection system are known as such and, therefore, need not be described in detail.

The pump P2 of the pump arrangement comprises additional pump means by which a reduction agent, as for example a hydrous solution of sodium tetrahydrideborate, is fed through a conduit R to a reduction flow-through reactor L4. The conduit R ends in the outlet conduit which goes out from the flow-through reactor L2 and leads to the reduction flow-through reactor L4. Therein, the supply of the reduction agent has to be rated taking into consideration the amount of unused disintegrating agent which is still present in the disintegrated sample. In addition in known way, an inert gas flow of argon enters the liquid flow which contains the disintegrated sample. When passing through the reduction flow-through reactor L4 the disintegrated sample is transformed with the reduction agent to form the gaseous products which then are conveyed by the inert gas flow Ar.

A gas-liquid separator GLS of known construction is connected downstream of the reduction flow-through reactor L4. In this gas-liquid separator the liquid flow is separated from the inert gas flow and is supplied to the waste vessel by the action of the pump P2. An aerosol trap F of known construction is connected to the output of this gas-liquid separator GLS.

In the case of the hydride analysis, the thus separated inert gas flow is supplied to known sample inlet means for the heatable quartz cuvette of the atomic absorption spectrometer AAS. In the case of the mercury determination, the inert gas flow is passed over a mercury adsorber known per se, by which the mercury is bound, for example, as amalgam. The mercury subsequently is expelled from this mercury adsorber by heating out in an inert gas flow and is supplied to the atomic absorption spectrometer AAS through known sample inlet means.

It has turned out that, in spite of the length of the flow path and in spite of the passage through the two flow-through reactors L2 and L4, the sensitivity of the measurement of the atomic absorption of the hydride former and the mercury is not affected, even though the dispersion, that means the mixture of the sample with the carrier liquid, is favoured by the above mentioned circumstances. It may be supposed that these negative effects are compensated for in that the liquid passing through flow-through reactor L2 still has a relatively high temperature. This very probably not only causes fast transformation of the disintegrated sample with the reduction agent, but causes also a particularly effective separation of the gaseous reduction products from the carrier liquid by the inert gas flow due to the favourable location of the gas-liquid solution equilibrium at the high temperature.

Figure 4B:
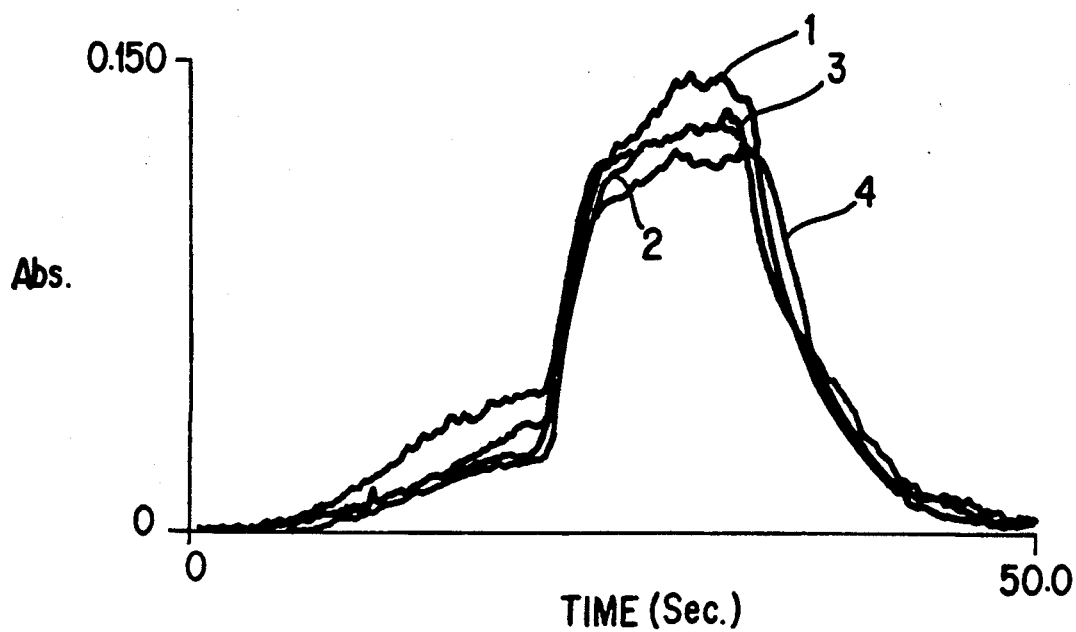
FIG. 4B shows the measuring signal waveforms of the four arsenic compounds of FIG. 4A, these measuring signal waveforms being obtained using the flow-injection system of FIG. 2.
Figure 4A:
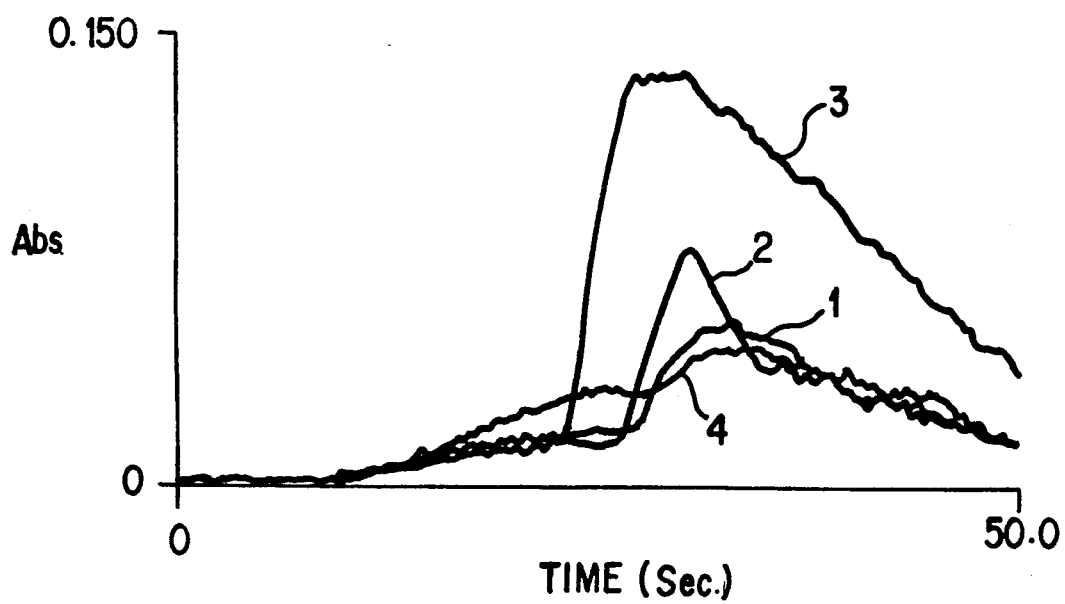
FIG. 4A shows the measuring signal waveforms of the atomic absorption of four arsenic compounds with different valence states of the arsenic, these measuring signal waveforms being obtained by the hydride method.

The above described flow-injection system can advantageously be used for determination of, for example, the total arsenic in a sample. With arsenic, the problem arises that the arsenic is present in different valence states, for example in different valencies or also in the form of arsenic-organic compounds. These different arsenic compounds are measured with different sensitivities. For example, measurements with samples, which contain 20 g/l of an arsenic compound in the form of trivalent arsenic (sodium meta-arsenite; Merck 6287), pentavalent arsenic (sodium hydrogen arsenate trihydrate; Merck 6284, disodic methylarsenate hexahydrate pharmapreparation "arrhenalum") and sodium dimethylarsenate hexahydrate, result in the conventional hydride atomic absorption measurement in the different measuring signal waveforms 1 to 4 which are illustrated in FIG. 4A. Accordingly, different quantities of the total arsenic would be found in a sample which contains more than one of these compounds depending on its composition.

The experiments described in the following and in the FIG. 4A and 4B have been carried out with a Perkin-Elmer PE 2100 atomic absorption spectrometer which is provided with the above mentioned FIAS-200 flow-injection system having AS-90 autosampler, FIA-mercury/hydride-arrangement and the above mentioned microwave oven. The sample loop L1, the flow-through reactor L2, the conduit coil L3 and the reduction flow-through reactor L4 comprise conduits of polytetrafluor ethylene. The sample loop L1 contains 2 ml sample for the mercury determination and 1 ml sample for the determination of hydride formers. The flow-through reactor L2 has a total length of 10.2 m, the conduit coil L3 has a total length of 2.3 m and the reduction flow-through reactor L4 has a total length of 10 cm (100 cm for the determination of selenium). The feed rate is 8.5 ml/min. for the carrier liquid flow. Under the mentioned circumstances, the total dwell time of the carrier liquid with the sample mixed with the disintegrating agent in the microwave oven MWD is 46 s, the dwell time in the radiation cavity being only 6,3 s. Overheating is ruled out under these conditions.

For the mercury determination according to the amalgam method, the aerosol trap F comprises a glass fiber filter (Satorius SM 134 00-50S) and, for the determination of the hydride formers, a polytetrafluor ethylene diaphragm (micropores 0.2μ, SU 7492 Gore-Tex).

An alkaline potassium peroxodisulphate solution (2 percent in weight in 0.4 M NaOH) serves as disintegrating agent for the samples containing arsenic. For the determination of bismuth, a bromate/bromidesolution in diluted hydrochloric acid (2.67 mM potassium bromate and 13.4 mM potassium bromide in 2 M HCl) is recommended as disintegrating agent. For the determination of tin, a similar bromate/bromide-solution (2.67 mM potassium bromate and 13.4 mM potassium bromide in 0.01 M HCl with 1% tartaric acid) or an acid peroxodisulphate solution 1 percent in weight of potassium peroxodisulphate in sulphuric acid (0.05 percent in volume) with 1% tartaric acid) is recommended as disintegrating agent. An acid peroxodisulphate solution (0.4 M ammonium peroxodisulphate, 0.015 M nitric acid, 0.01 M acetic acid) is recommended as disintegrating agent for lead, and an acid bromate/bromide-solution (1.33 mM potassium bromate, 6.72 mM potassium bromide in hydrochloric acid (3.2 percent in volume) with stabilizer, namely 50 mg/l potassium dichromate in 0.33 percent in volume of nitric acid) is recommended as disintegrating agent for mercury.

When using the above described flow-injection system, the above mentioned problems due to the different valence states of the arsenic do not arise. The measuring signal waveforms obtained with the above mentioned individual arsenic compounds are illustrated in FIG. 4B. It can be seen that all of the investigated arsenic compounds result in approximately identical measuring signal waveforms. Actually, a measuring signal waveform of a sample which contains all of the above mentioned arsenic compounds in the same total quantity, falls in the range of the illustrated measuring signal waveforms and can hardly be distinguished therefrom. Therefore, the flow-injection system also permits an exact total determination of elements which are usually present in the sample in different valence states.

We claim:

1. A system for disintegrating samples and for supplying the disintegrated samples to an analytical instrument, comprising
   a microwave oven having a radiation cavity and containing a flow-through reactor having an inlet and an outlet,
   pump means for pumping a mixture of sample and a disintegrating agent through said flow-through reactor,
   said reactor outlet being adapted to be connected to sample inlet means of said analytical instrument,
   said flow-through reactor including a flow-through conduit coil having a plurality of turns,
   each turn of said flow-through conduit coil having a first portion of its length extending into said radiation cavity and a second portion located outside said radiation cavity, so that said mixture of sample and disintegrating agent flowing through said flow-through conduit coil alternatingly passes a plurality of times inside said radiation cavity, where it is heated by the microwave energy of said oven, and outside said radiation cavity, where it is not heated.

2. A system as claimed in claim 1 wherein the conduit of said flow-through conduit coil extends substantially transverse to a beam of microwave radiation in said microwave oven.

3. A system as claimed in claim 2 further comprising a ballast conduit coil arranged in said radiation cavity, and means for pumping a microwave-absorbing fluid through said ballast conduit coil.

4. A system as claim in claim 3 wherein said conduit of said ballast conduit coil extends substantially parallel to said beam of microwave radiation in said microwave oven.

5. A system as claimed in claim 4 wherein said flow-through conduit coil is wound on an elongated conduit carrier, a first portion of the length of said carrier extends into said radiation cavity of the microwave oven and a second portion of the length of the carrier being arranged outside the radiation cavity, said second portion being longer than said first portion, said carrier having a substantially rectangular cross section, the circumference of the cross section of the first portion being less than the circumference of the cross section of the second portion, said ballast conduit coil being wound about the circumference of the cross section of the first portion of the carrier inside said conduit coil of the flow-through coil.

6. A system as claimed in claim 5, wherein said conduit carrier consists of polytetrafluorethylene.

7. A system as claimed in claim 1, wherein the microwave oven comprises programmable adjusting means for adjusting the heating power and the heating period.

8. A system as claimed in claim 1, wherein said analytical instrument is an atomic spectrometer.

9. A system as claimed in claim 8, wherein said atomic spectrometer is an atomic absorption spectrometer.

10. A system as claimed in claim 9, and further comprising
   (a) a reduction flow-through reactor having an inlet and an outlet, said inlet of said reduction flow-through reactor communicating with the outlet of said flow-through reactor in said microwave oven, and
   (b) means for supplying a reducing agent to said inlet of said reduction flow-through reactor, said outlet of said reduction flow-through reactor being adapted to be connected to sample inlet means of said atomic spectrometer.

11. A system as claimed in claim 10 and further comprising means for supplying an inlet gas flow to said reduction flow-through reactor.

12. A system as claimed in claim 11 and further comprising an aerosol trap interconnected between said outlet of said reduction flow-through reactor and said sample inlet means.

13. A system as claimed in claim 12, and further comprising a mercury absorber interconnected between said aerosol trap and said sample inlet means.

14. A system as claimed in claim 1, and further comprising flow-injection means for injecting sample liquid into a flow of carrier liquid, said flow of carrier liquid being pumped by said pump means through said flow-through reactor.

* * * * *